United States Patent
Barty

(10) Patent No.: US 10,508,998 B2
(45) Date of Patent: Dec. 17, 2019

(54) METHODS FOR 2-COLOR RADIOGRAPHY WITH LASER-COMPTON X-RAY SOURCES

(71) Applicant: Lawrence Livermore National Security, LLC, Livermore, CA (US)

(72) Inventor: Christopher P. J. Barty, Hayward, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 97 days.

(21) Appl. No.: 15/319,986

(22) PCT Filed: May 7, 2015

(86) PCT No.: PCT/US2015/029737
§ 371 (c)(1),
(2) Date: Dec. 19, 2016

(87) PCT Pub. No.: WO2015/171923
PCT Pub. Date: Nov. 12, 2015

(65) Prior Publication Data
US 2017/0241920 A1    Aug. 24, 2017

Related U.S. Application Data

(63) Continuation-in-part of application No. 14/274,348, filed on May 9, 2014, now Pat. No. 9,706,631.
(Continued)

(51) Int. Cl.
*A61B 6/00* (2006.01)
*G01N 23/087* (2018.01)
(Continued)

(52) U.S. Cl.
CPC ............ *G01N 23/087* (2013.01); *A61B 6/06* (2013.01); *A61B 6/405* (2013.01); *A61B 6/4241* (2013.01);
(Continued)

(58) Field of Classification Search
CPC ............ A61B 6/481; G01N 2223/206; G01N 2223/423; G01N 23/087
See application file for complete search history.

(56) References Cited

U.S. PATENT DOCUMENTS 3,780,294 A    12/1973 Sowerby
3,854,049 A    12/1974 Mistretta et al.
(Continued)

FOREIGN PATENT DOCUMENTS

EP        0600673 A2    6/1994
JP     2007195888 A    8/2007
(Continued)

OTHER PUBLICATIONS

International Search Report and Written Opinion of the International Searching Authority for PCT/US2015/029737, dated Aug. 17, 2015; ISA/KR.
(Continued)

*Primary Examiner* — Dani Fox
(74) *Attorney, Agent, or Firm* — John P. Wooldridge

(57) ABSTRACT

High-contrast, subtraction, x-ray images of an object are produced via scanned illumination by a laser-Compton x-ray source. The spectral-angle correlation of the laser-Compton scattering process and a specially designed aperture and/or detector are utilized to produce/record a narrow beam of x-rays whose spectral content consists of an on-axis region of high-energy x-rays surrounded by a region of slightly lower-energy x-rays. The end point energy of the laser-Compton source is set so that the high-energy x-ray region contains photons that are above the k-shell absorption edge (k-edge) of a specific contrast agent or specific material within the object to be imaged while the outer region consists of photons whose energy is below the k-edge of the same contrast agent or specific material. Scanning the illumination and of the object by this beam will simultaneously
(Continued)

record and map the above edge and below k-edge absorption response of the object.

28 Claims, 14 Drawing Sheets

Related U.S. Application Data

(60) Provisional application No. 61/990,642, filed on May 8, 2014, provisional application No. 61/990,637, filed on May 8, 2014.

(51) Int. Cl.
*H05G 2/00* (2006.01)
*A61B 6/06* (2006.01)
*G21K 1/02* (2006.01)
*G21K 1/04* (2006.01)

(52) U.S. Cl.
CPC .............. *A61B 6/481* (2013.01); *A61B 6/482* (2013.01); *G21K 1/02* (2013.01); *G21K 1/043* (2013.01); *H05G 2/00* (2013.01); *H05G 2/008* (2013.01); *G01N 2223/206* (2013.01); *G01N 2223/408* (2013.01); *G01N 2223/423* (2013.01); *G01N 2223/501* (2013.01)

(56) References Cited

U.S. PATENT DOCUMENTS

| | | |
|---|---|---|
| 4,598,415 A | 7/1986 | Luccio et al. |
| 4,843,619 A | 6/1989 | Sheridan |
| 5,040,200 A | 8/1991 | Ettinger et al. |
| 5,115,459 A | 5/1992 | Bertozzi |
| 5,247,562 A | 9/1993 | Steinbach |
| 5,293,414 A | 3/1994 | Ettinger et al. |
| 5,323,004 A | 6/1994 | Ettinger et al. |
| 5,353,291 A | 10/1994 | Sprangle et al. |
| 5,420,905 A | 5/1995 | Bertozzi |
| 5,847,863 A | 12/1998 | Galvanauskas et al. |
| 6,035,015 A | 3/2000 | Ruth et al. |
| 6,442,233 B1 | 8/2002 | Grodzins et al. |
| 6,661,818 B1 | 12/2003 | Feldman et al. |
| 6,684,010 B1 | 1/2004 | Morris, Jr. et al. |
| 6,687,333 B2 | 2/2004 | Carroll et al. |
| 7,060,983 B2 | 6/2006 | Turner |
| 7,120,226 B2 | 10/2006 | Ledoux et al. |
| 7,277,526 B2 | 10/2007 | Rifkin et al. |
| 7,391,850 B2 | 6/2008 | Kaertner et al. |
| 7,564,241 B2 | 7/2009 | Barty et al. |
| 7,596,208 B2 | 9/2009 | Rifkin et al. |
| 7,693,262 B2 | 4/2010 | Bertozzi et al. |
| 8,369,480 B2 | 2/2013 | Barty |
| 8,487,285 B2 | 7/2013 | Matsumoto et al. |
| 8,693,637 B2 | 4/2014 | Lee et al. |
| 8,934,608 B2 | 1/2015 | Barty |
| 9,706,631 B2 | 7/2017 | Barty |
| 2002/0057760 A1 | 5/2002 | Carroll et al. |
| 2002/0097832 A1 | 7/2002 | Kaiser et al. |
| 2004/0109532 A1 | 6/2004 | Ford et al. |
| 2004/0159803 A1 | 8/2004 | Akselrod et al. |
| 2004/0240037 A1 | 12/2004 | Harter |
| 2005/0179911 A1 | 8/2005 | Boomgarden et al. |
| 2005/0226278 A1 | 10/2005 | Gu et al. |
| 2006/0166144 A1 | 7/2006 | Te Kolste et al. |
| 2006/0188060 A1 | 8/2006 | Bertozzi et al. |
| 2006/0193433 A1 | 8/2006 | Ledoux et al. |
| 2006/0249685 A1 | 11/2006 | Tanaka |
| 2006/0251217 A1 | 11/2006 | Kaertner et al. |
| 2007/0177640 A1 | 8/2007 | Liu |
| 2007/0263767 A1 | 11/2007 | Brondo |
| 2009/0045355 A1 | 2/2009 | Desbrandes |
| 2009/0052621 A1* | 2/2009 | Walter ................ A61B 5/4869 378/53 |
| 2009/0147920 A1 | 6/2009 | Barty et al. |
| 2009/0147922 A1 | 6/2009 | Hopkins |
| 2010/0061504 A1 | 3/2010 | Proksa |
| 2011/0007760 A1 | 1/2011 | Clowes et al. |
| 2011/0064200 A1 | 3/2011 | Bertozzi et al. |
| 2012/0288065 A1 | 11/2012 | Graves et al. |
| 2014/0028714 A1 | 1/2014 | Keating et al. |
| 2014/0328457 A1 | 11/2014 | Stutman et al. |

FOREIGN PATENT DOCUMENTS

| | | |
|---|---|---|
| JP | 2012173076 A | 9/2012 |
| WO | 2005081017 A1 | 9/2005 |
| WO | 2007038527 A1 | 4/2007 |
| WO | WO-2008022216 A2 | 2/2008 |
| WO | 2009086503 A1 | 7/2009 |
| WO | 2009097052 A1 | 8/2009 |
| WO | 2011071563 A1 | 6/2011 |

OTHER PUBLICATIONS

International Search Report and Written Opinion of the ISA for PCT/US2015/029742, ISA/KR, Daejeon, dated Aug. 19, 2015.
Chinese Office Action and Search Report for Chinese Patent Application No. 201580036385 dated Jul. 26, 2017, 12 pp.
Boucher, S., et al., "Inverse compton scattering gamma ray source", Nuclear Instruments and Methods in Physics Research, A 608, 2008, pp. S54-S56.
Gibson, D.J., et al., "Design and operation of a tunable MeV-level Compton-scattering-based x-ray source", The Americal Physical Society, Physical Review and Special Topics—Accelerators and Beams, 13, 2010, 12 p.
Hagmann, C.A., et al., "Transmission-based detection of nuclides with nuclear resonance fluorescence using a quasimonoenergetic photon source", J. Appl. Phys., vol. 106, 2009, pp. 1-7.
Jovanovic, I, et al., "High-power picosecond pulse recirculation for inverse compton scattering", Nuclear Physics B, 184, 2008, pp. 289-294.
Shverdin, M.Y., et al., "High-power picosecond laser pulse recirculation", Optics Letters, vol. 35, No. 13, 2010, pp. 2224-2226.
Zamfir, N.V., et al., "Extreme light infrastructure: nuclear physics", Proc. of SPIE, vol. 8080, pp. 1-8.
International Search Report and Written Opinion for PCT/US12/054872 related to U.S. Appl. No. 14/343,706, 9 pages.
International Search Report and Written Opinion for PCT/US12/047483 related to U.S. Appl. No. 13/552,610, 9 pages.
First Examination Report for corresponding New Zealand Application No. 727182, dated May 11, 2017, 7 pp.
Communication persuant to Article 94(3) EPC for EP Application No. 15789809.9-1124, European Patent Office, dated Mar. 18, 2019.

* cited by examiner

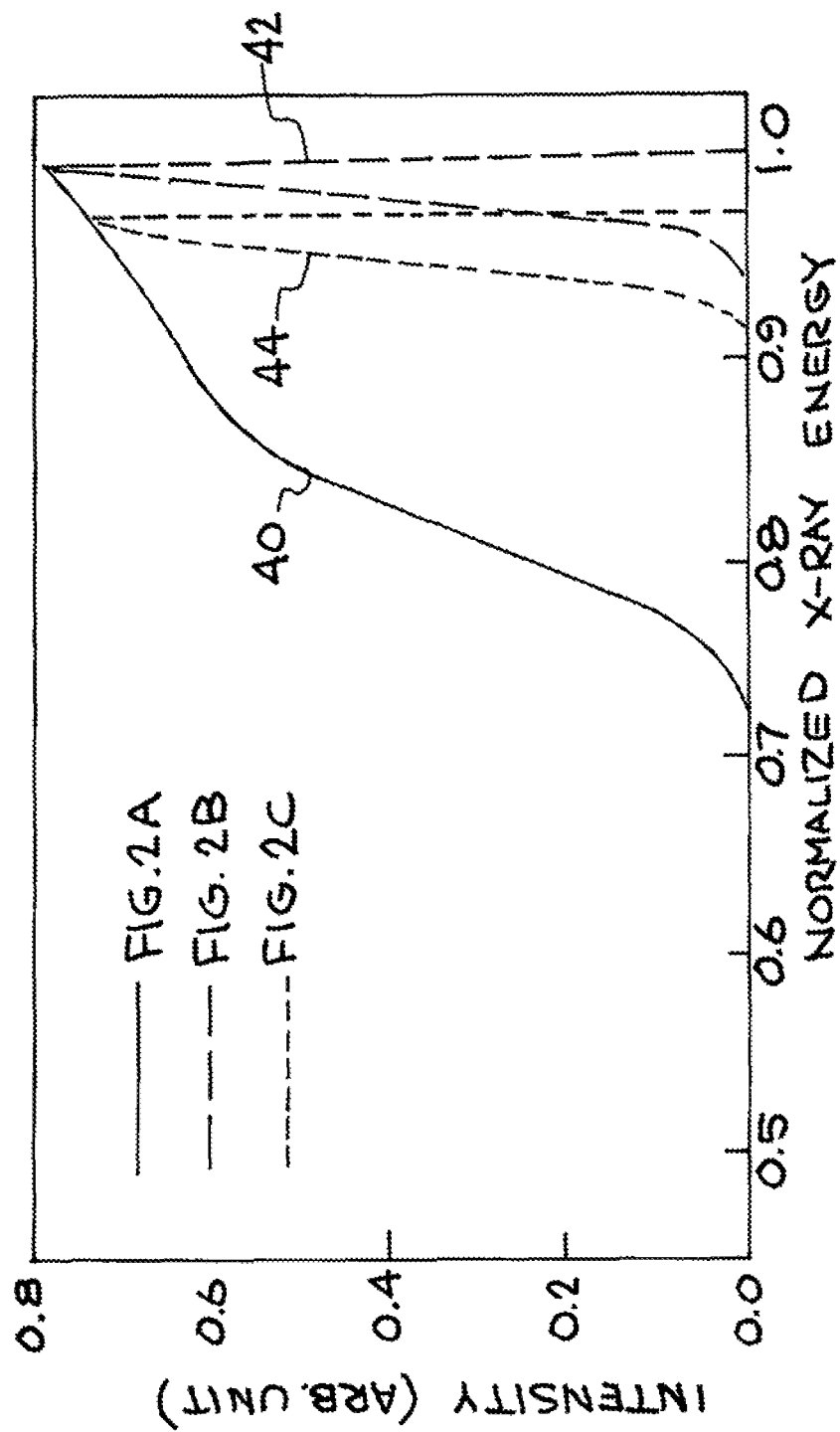

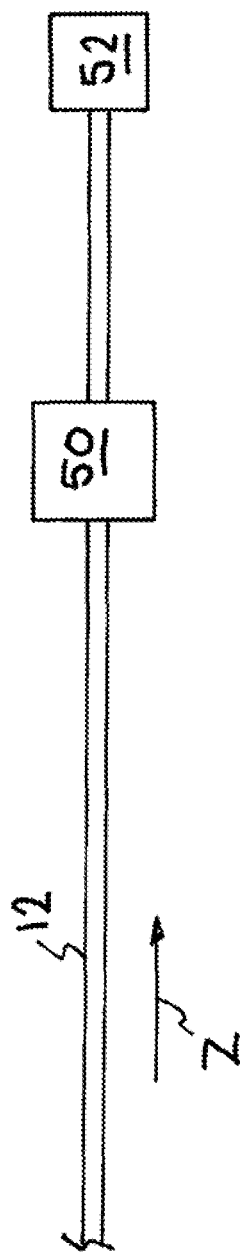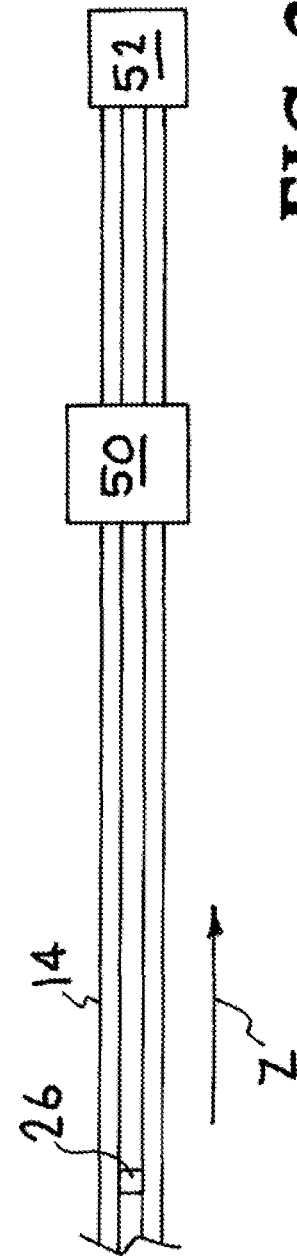

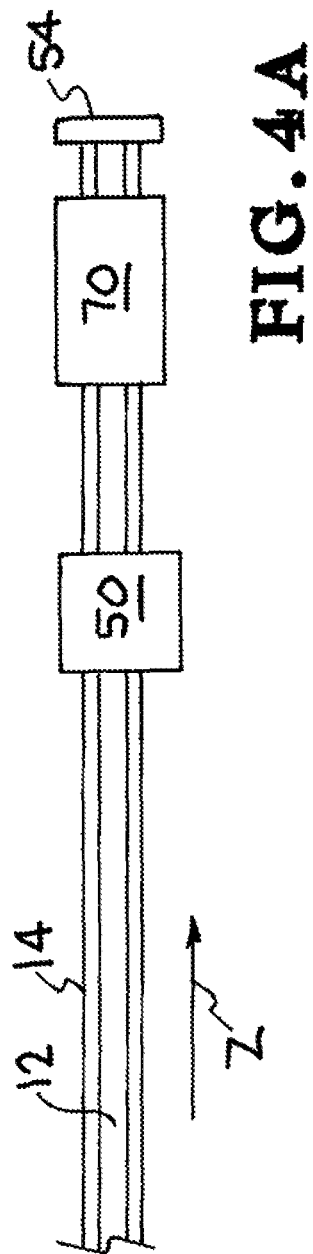
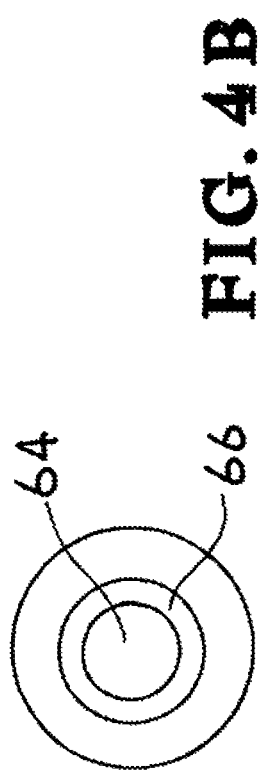

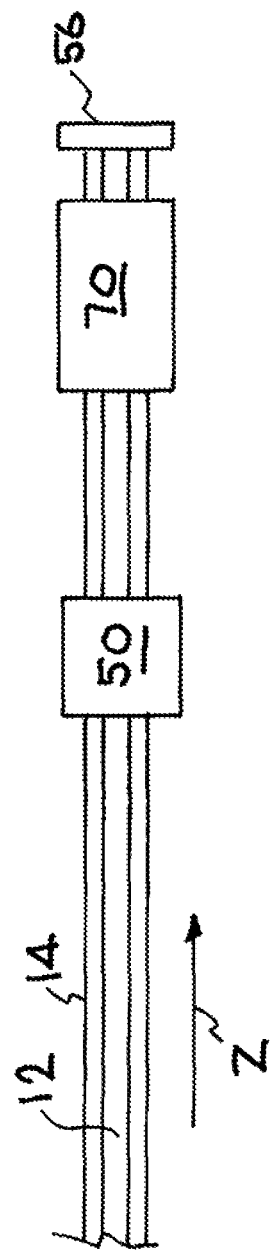

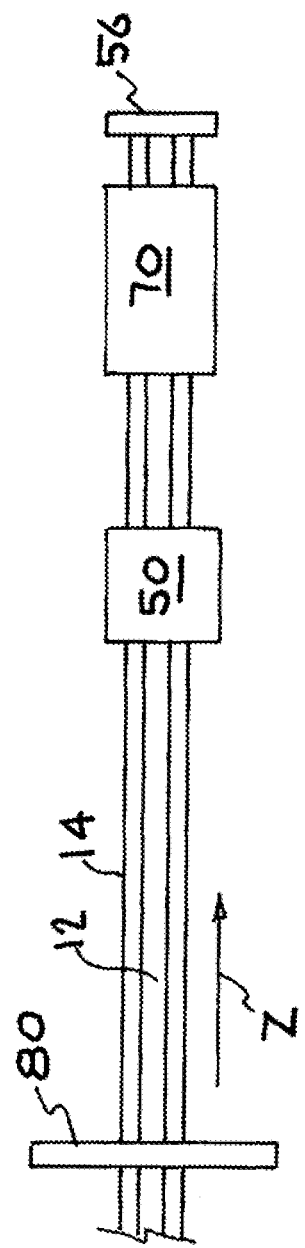

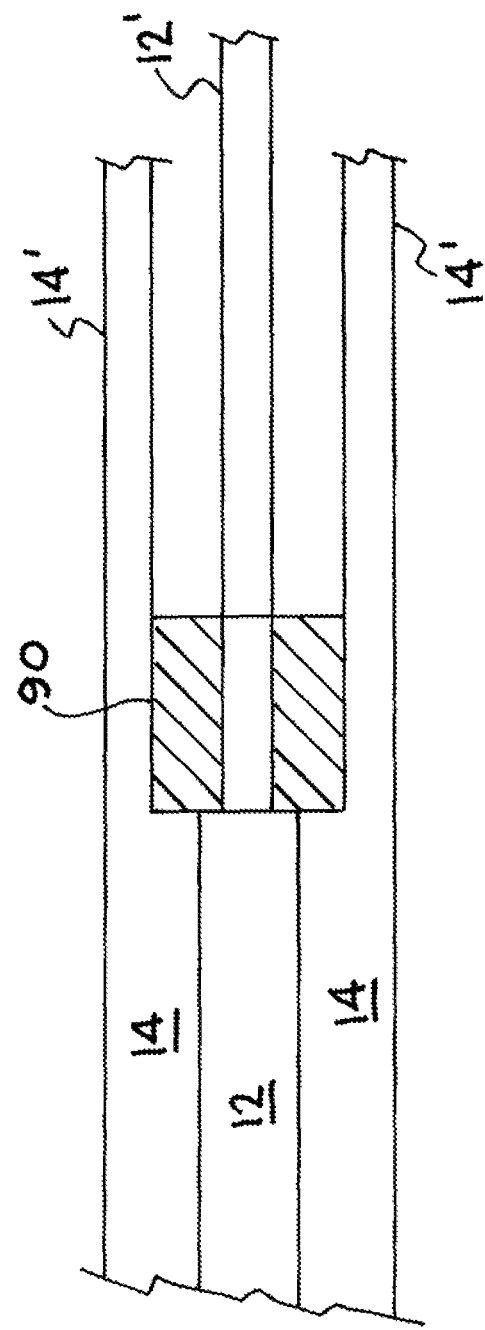

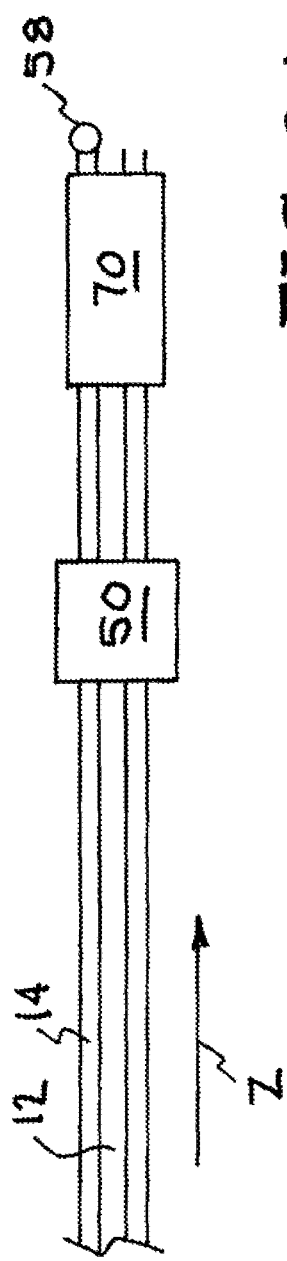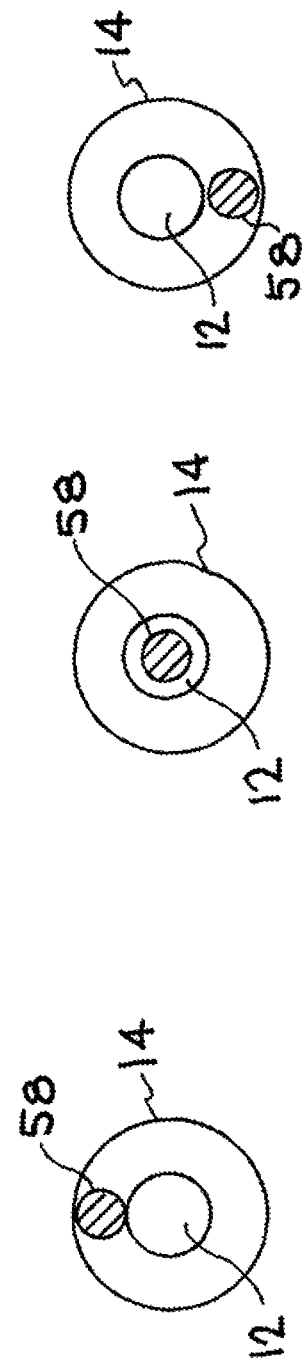

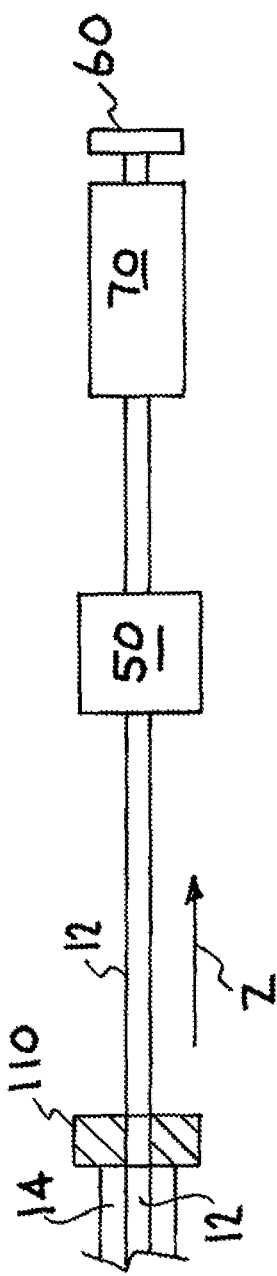
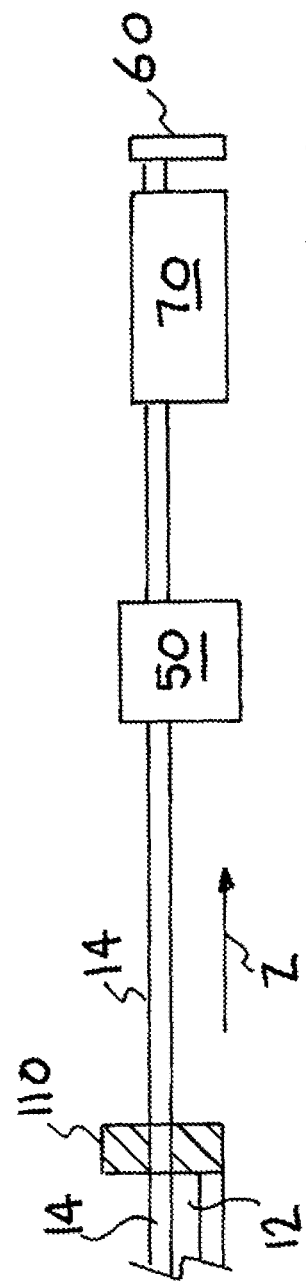

METHODS FOR 2-COLOR RADIOGRAPHY WITH LASER-COMPTON X-RAY SOURCES

CROSS-REFERENCE TO RELATED APPLICATIONS

This application claims the benefit of U.S. Provisional application 61/990,642, titled "Two-Color Radiography System and Method with Laser-Compton X-Ray Sources", filed on May 8, 2014 and incorporated herein by reference. This is a continuation-in-part of U.S. patent application Ser. No. 14/274,348 titled "Modulated Method for Efficient, Narrow-Bandwidth, Laser Compton X-Ray and Gamma-Ray Sources," filed May 9, 2014, incorporated herein by reference. U.S. patent application Ser. No. 14/274,348 claims the benefit of U.S. Provisional Patent Application No. 61/821,813 titled "Modulated, Long-Pulse Method for Efficient, Narrow-Bandwidth, Laser Compton X-Ray and Gamma-Ray Sources," filed May 10, 2013, incorporated herein by reference. U.S. patent application Ser. No. 14/274, 348 claims the benefit of U.S. Provisional application 61/990,637, titled "Ultralow-Dose, Feedback Imaging System and Method Using Laser-Compton X-Ray or Gamma-Ray Source", filed May 8, 2014 and incorporated herein by reference. U.S. patent application Ser. No. 14/274,348 claims the benefit of U.S. Provisional application 61/990, 642, titled "Two-Color Radiography System and Method with Laser-Compton X-Ray Sources", filed on May 8, 2014 and incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

Field of the Invention

The present invention relates to x-ray and gamma-ray generation via laser Compton scattering and more specifically, it relates to subtraction radiology utilizing laser-Compton x-ray sources.

Description of Related Art

In conventional 2-D x-ray/gamma-ray imaging, the patient or object is illuminated with a flat field of x-rays or gamma-rays and the transmitted signal is recorded on a 2D film or array of detectors. Variations of material density within the object cause variations in beam transmission for the penetrating radiation and these variations appear as shadows on film or a detector array. The dynamic range of this imaging technique is determined by the response function of the detector system and by the object thickness and secondary x-ray scattering by the object. In addition, all parts of the object see the same input flux (photons per unit area) and the total dose impinging upon the object is set by the area of the object and by the flux required to penetrate the densest region of the object, i.e., the flux required to resolve the structures of interest within the object. In this imaging modality, the entire object sees a high dose.

For some imaging procedures in which the desired object is either small or low density, a higher atomic number contrast agent is injected or ingested to provide specific information about targeted structures. For example in coronary angiography the goal is to image the blood vessels and in particular to locate areas of reduced blood vessel aperture or blockages. Because the blood and the blood vessels are soft tissue and small in size, the total x-ray attenuation by them is small compared to the background matrix in which they are present and thus it is hard if not impossible to sufficiently resolve them in a conventional, whole body x-ray image. To overcome this issue, a dense material generally of higher atomic number than the surrounding biological material is injected into the blood stream to increase the x-ray attenuation in the areas of interest and in doing so improve contrast. Contrast agents used in human imaging tasks must of course be certified as being biologically inert or at least relatively so. For coronary angiography, iodine-containing compounds have been used as contrast agents. It should be noted that while this procedure does improve contrast and provide the required spatial information, the dose received by the patient can be very high. Some coronary angiography procedures can expose the patient to a full year's allowable dose.

In order to increase the contrast and/or reduce the required dose for an image at a desired contrast level, two-color subtraction imaging has been suggested and demonstrated. In this modality, the patient is illuminated twice with a tunable, quasi-mono-energetic x-ray source. In one case the x-ray source has its energy set slightly above the k-shell absorption edge of the contrast agent and in the other case it is set slightly below. As shown in FIG. 1, the absorption cross section for the contrast material varies dramatically around the k-shell absorption region while the absorption cross section for the surrounding material can be relatively unchanged. If the two images are normalized to have the same signal in regions not containing the contrast agent, then a subtraction of the normalized images will be an image whose content is due primarily to the contrast agent.

While early experiments conducted with filtered light from synchrotron x-ray sources demonstrated that this procedure could dramatically increase image contrast and/or reduce dose to the patient, its implementation in real-world clinical environments has been relatively limited due to the lack of clinically-compatible, quasi-mono-energetic x-ray sources. Synchrotron sources are expensive (>$100M), large (>100 m in diameter) and relatively uncommon. In addition the output from a synchrotron source is constant and not rapidly adjustable nor easily scanned across the object.

It should also be noted that some have attempted to use conventional bremsstrahlung sources for k-edge imaging by changing the end point energy of the electron beam impinging upon the rotating anode so that the highest energy photons are either above or slightly below the desired k-edge absorption. In practice this, however, does not work very well as the total x-ray content of a bremsstrahlung source extends from the end point energy of the electron beam to DC, thus the fraction of the beam spectrum that is above the k-edge is relatively small compared to the total x-ray production and the image is thus dominated by background absorption. The dose to the patient is also high in this mode as it predominantly comes from the low energy tail of the bremsstrahlung spectrum of the source. To some extent this issue can be minimized by attenuating the beam with a low atomic number material that preferentially reduces the low energy portion of the spectrum relative to the high-energy portion but this of course reduces the total x-ray flux available for imaging, increases the proportion of image-degrading, scattered x-ray content within the illuminating x-ray beam and requires a higher current anode device to create the same number of useful above and below k-edge photons at the object.

Note that the k-shell edge and not the outer shell absorption edges, i.e. L and M is generally used for two color clinical imaging as the x-ray energy required to remove a k-shell electron generally falls in the x-ray region of interest to clinical radiography while the outer shell absorptions occur at lower x-ray energies. The same two-color image subtraction scheme can be implemented, however, at lower energies using outer shell absorption edges if object and source are compatible.

SUMMARY OF THE INVENTION

A new method for creation of high-contrast, subtraction, x-ray images of an object via scanned illumination by a laser-Compton x-ray source is described. The invention utilizes the spectral-angle correlation of the laser-Compton scattering process and a specially designed aperture and/or detector to produce/record a narrow beam of x-rays whose spectral content consists of an on-axis region of high-energy x-rays surrounded by a region of slightly lower-energy x-rays. The end point energy of the laser-Compton source is set so that the high-energy x-ray region contains photons that are above the k-shell absorption edge (k-edge) of a specific contrast agent or specific material within the object to be imaged while the outer region consists of photons whose energy is below the k-edge of the same contrast agent or specific material. Illumination of the object by this beam will simultaneously record the above k-edge and below k-edge absorption response of the object for the regions illuminated by the respective portions of the beam. By either scanning the beam or scanning the object relative to the beam, one may build up the full above and below k-edge spatial response of the object. These spatial responses when properly-normalized and subtracted from one another create a map that is sensitive to the presence or absence of the specific contrast agent or special material within the object and as such the subtraction image represents a high-contrast radiograph of the presence of the contrast agent or special material within the object.

The technique may be used for a variety of x-ray imaging tasks to either increase image contrast at a fixed x-ray dose to the object or to reduce the x-ray dose required to obtain an x-ray image of a desired contrast. Of particular note is that this method obtains both the above and below k-edge maps of the object without requiring any adjustment of the end-point energy of the x-ray source or any whole beam filtering of the x-ray source and can do so without illuminating the object with lower-energy, non-penetrating x-rays that are typically present from conventional rotating anode, x-ray sources. Possible applications include but are not limited to coronary angiography in which the blood is doped with iodine as a contrast agent and used to provide an image of arterial blockages or low-dose mammography in which the breast is injected with a gadolinium based contrast agent and used to image the vascularization associated with pre-cancerous material. In both cases, subtraction x-ray images of the contrast agents can provide vital information and do so with equivalent or better image quality and/or significantly lower dose than conventional x-ray radiography.

The invention has a wide variety of uses including high-contrast x-ray imaging, medical x-ray imaging, e.g., angiography and mammography, subtraction x-ray imaging of specific atomic species in an object or patient and non-destructive evaluation of multi-component parts with x-rays e.g., element specific radiography of computer chips and components.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 2D shows the angle correlated spectra from the aperture beams of FIGS. 2A-2C FIG. 3A shows a configuration for imaging an above k-edge laser-Compton x-ray source.

FIG. 3B shows a configuration for imaging a below k-edge laser-Compton x-ray source.

FIG. 4A illustrates an embodiment of a two pixel modality of the present invention.

FIG. 4B illustrates an embodiment of a two pixel detector for use with the two pixel modality of FIG. 4A.

FIG. 5A illustrates a "many pixel" modality embodiment of the present invention.

FIG. 6A illustrates an "equal spatial dimension" modality embodiment of the present invention where the beam is passed through a slit so that either the horizontal or vertical dimensions of the beam portions are equal.

FIG. 7A illustrates a "discontinuous annular beam" modality embodiment of the present invention where the beam is a set of apertures/beam blocks that produce distinct annular beams with high and low energy x-ray content.

FIG. 7C shows an enlarged view of annular beam block 90 located in the x-ray beam.

FIG. 8A shows a "dithered detector" modality according to the present invention.

FIGS. 8B-D shows various positions of a detector in the beam of the embodiment of FIG. 8A.

FIGS. 9A and 9B show a "dithered aperture" modality according to the present invention.

DETAILED DESCRIPTION OF THE INVENTION

Figure 1:
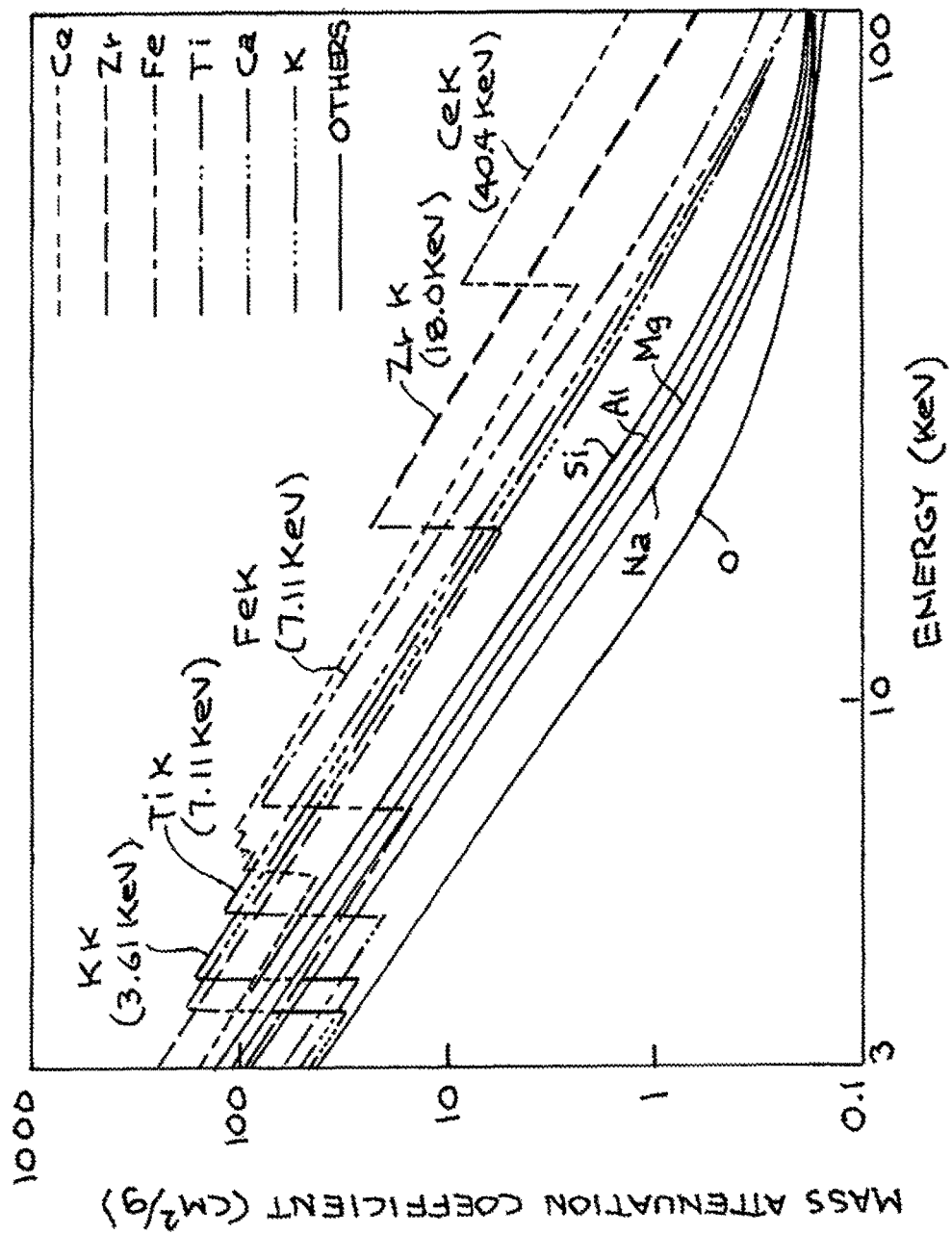
FIG. 1 shows the k-edge absorption coefficient versus energy for various elements.

In this invention, the laser-Compton scattering process is used to create a beam of x-rays that consists of two distinct spatial regions with two distinct x-ray spectra; one region on axis having higher energy photons and another region surrounding it having lower energy photons. This beam is then used in a scanning imaging modality to produce a 2-color, subtraction, x-ray image of an object. For appropriate settings of the laser-Compton x-ray beam energy, this subtraction image will be highly sensitive only to the presence of specific materials within the radiographed object. This high-contrast, low-dose image is obtained without adjustment to the laser-Compton x-ray source end point energy, i.e., without tuning the x-ray source.

Laser-Compton scattering (sometimes also referred to as inverse Compton scattering) is the process in which an energetic laser pulse is scattered off of a short duration bunch of relativistic electrons. This process has been recognized as a convenient method for production of short duration bursts of quasi-mono-energetic, x-ray and gamma-ray radiation. When interacting with the electrons, the incident laser light induces a transverse motion of the electrons within the bunch. The radiation from this motion when observed in the rest frame of the laboratory appears to be a forwardly directed, Doppler upshifted beam of high-energy photons. For head on collisions, the full spectrum of the laser-Compton source extends from DC to 4 gamma squared times the energy of the incident laser, where Gamma is the normalized energy of the electron beam, i.e., gamma=1 when Electron energy?=511 keV. The end point energy of the laser-Compton source may be tuned, by changing the energy of the electron bunch and/or the energy of the laser photons. Beams of high-energy radiation ranging from a few keV to greater than a MeV have been produced by this process and used for a wide range of applications.

The spectrum of the radiated Compton light is highly angle-correlated about the propagation direction of the electron beam with highest energy photons emitted only in the forward direction. See FIG. 2. With an appropriately designed aperture placed in the path of the laser-Compton beam, one may easily create a quasi-mono-energetic x-ray or gamma-ray beam whose bandwidth (DE/E) is typically 10% or less.

Laser-Compton x-ray sources are also highly collimated especially in comparison with conventional rotating anode x-ray or gamma-ray bremsstrahlung sources. The cone angle for emission of the half-bandwidth spectrum of a laser-Compton source is approximately 1 radian on gamma or of order of milliradians and the cone angle for narrowest bandwidth, on-axis portion of the spectrum may be of order of 10's of micro-radians. Typical rotating anode sources have beam divergences of ~0.5 radians. This high degree of collimation makes laser-Compton x-ray sources ideally suited to pixel by pixel imaging modalities.

Furthermore, the output from a laser-Compton x-ray source is dependent upon the simultaneous presence of laser photons and electrons at the collision point (the interaction point). Removal of either eliminates the output of the source completely thus making it easy for one to rapidly turn on or off the x-ray or gamma-ray output.

As illustrated in FIGS. 2A-2D, this invention utilizes two regions of the angle-correlated spectral output of a laser-Compton x-ray beam; the on axis portion of the beam containing the highest energy photons and the region immediately around this portion of the beam containing photons of lower energy. The extent of the surrounding region, the spectral content of the surrounding region and the total number of photons in the surrounding region relative to the on axis portion of the beam may be easily set by passing the entire beam through an appropriate aperture and/or beam blocks of fixed size. By operating the laser-Compton x-ray source with fixed laser pulse energy and fixed electron bunch charge, the total output of the laser-Compton x-ray source as well as the ratio of total x-ray photons in the two regions of interest can be held fixed and constant.

Figure 2A:
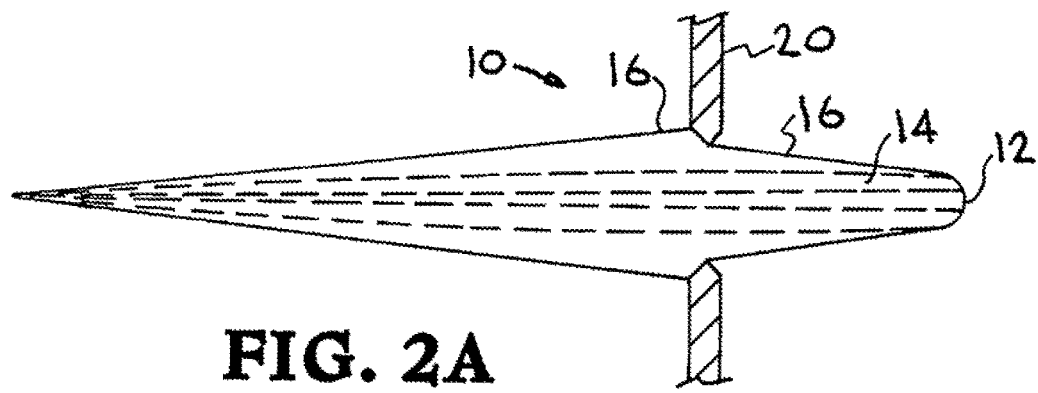
FIG. 2A shows a loosely-apertured, wide-bandwidth spectrum for a beam from an apertured laser-Compton x-ray source.
Figure 2B:
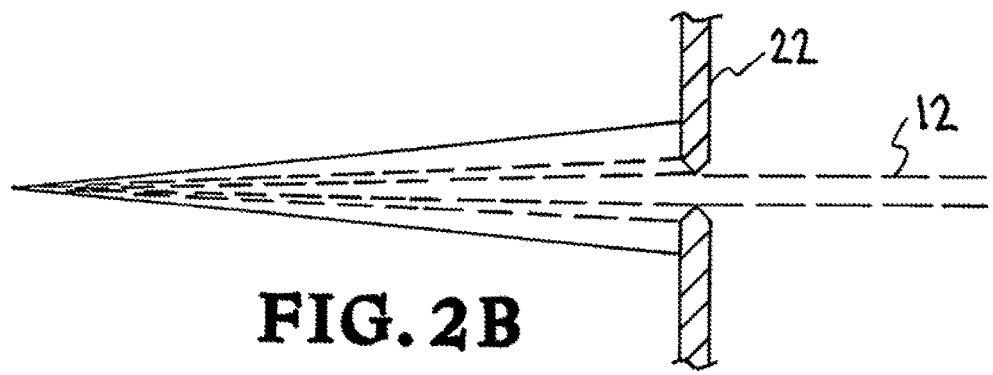
FIG. 2B shows a on-axis, high-energy narrow-band spectrum for a beam from an apertured laser-Compton x-ray source.
Figure 2C:
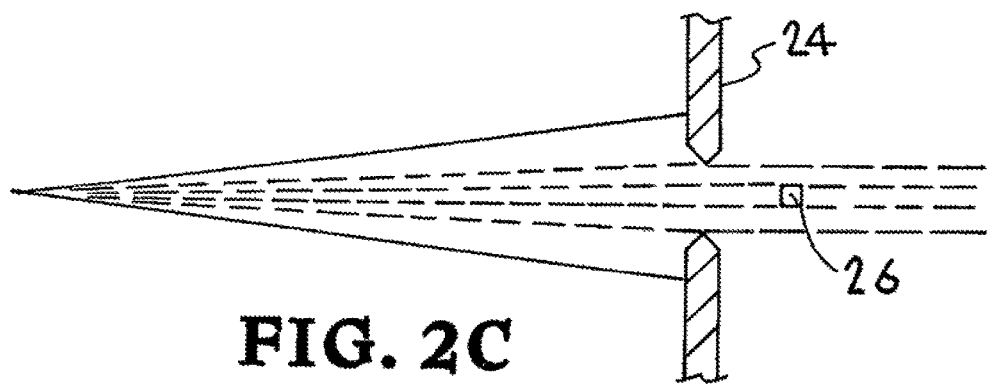
FIG. 2C shows a narrow-band, lower energy spectrum surround an on-axis spectrum for a beam from an apertured laser-Compton x-ray source.

Specifically, FIG. 2A shows a cross-sectional side view of a diverging output beam 10 from a laser-Compton x-ray source. The cross-section is taken in the plane of the page through the center of the beam 10. In the following discussions, the term "axis" refers to the central optical axis on which beam 10 propagates. The energy of beam 10 is highest in the central on-axis region 12 and falls off with radial distance of the beam relative to the central axis. Thus, region 14 has less energy than region 12 and region 16 has less energy that region 14. Although the regions are shown in FIGS. 2A, 2B and 2C to have distinct lines of separation one to another, in reality, there is a continuous change of energy from the most energetic beam at the very center to the lowest energy at the outer radius. The figure includes a cross-sectional view of a circular aperture 20. In FIG. 2A, aperture 20 has an opening diameter that allows regions 12 and 14 to pass and that blocks a large portion of region 16, although a small portion is allowed through. The area under the curve 40 of FIG. 2D is the loosely-apertured, wide-bandwidth spectrum of light (x-ray energy) of the combination of energies of the portions of beam regions 12, 14 and 16. FIG. 2B illustrates the use of a narrow diameter aperture 22. The area under curve 42 of FIG. 2D represents the on-axis, high-energy narrow-band spectrum of only beam region 12. FIG. 2C illustrates the use of an aperture 24 that has a diameter that allows passage of beam regions 12 and 14 but not region 16. A beam block 26 is positioned to block beam region 12 and thus, only region 14 can propagate toward a target. Note that the beam 14 is shown in side view and the therefore the beam is really circular with a central area that has no energy because beam region 12 has been blocked by aperture 26. Thus, the area under curve 44 of FIG. 2D represents the narrow-band, lower-energy spectrum of only beam region 14. Note that many of the exemplary embodiments described herein utilize circular apertures, but the invention is not limited to a particular aperture shape. The exact transmitted spectrum will depend upon the shape and size of the aperture and/or beam block and the polarization of the laser.

To produce a 2-color, subtraction, x-ray image, the narrow-divergence, laser-Compton x-ray beam is either scanned across the object or the object is raster scanned relative to a fixed beam or a combination of scanning the beam and the object. For illustrative purposes (see FIGS. 3A and 3B), it is assumed that the beam is fixed and propagates in the z-direction and that the object is raster scanned in the x-y plane. The goal of a 2-color subtraction image is to detect within this object the presence of a specific atomic material that either occurs naturally or has been artificially added as a contrast agent. The beam energy for the laser-Compton source is chosen so that the on-axis, high-energy x-ray beam photons are above the k-shell absorption edge of the atomic material/contrast agent and the outside, surrounding, low-energy x-ray beam photons are below the k-shell absorption threshold. For each location in the scan, the transmitted x-ray beam impinges upon an electronic x-ray-sensitive detector that is aligned with the x-ray beam and held fixed in space with respect to the x-ray beam. The detector records separately and the number of ballistic photons impinging upon it from the inner and outer portions of the x-ray beam. After fully scanning the object, both the inner and outer portions of the beam will each have exposed the full 2-dimentional extent of the object. The recording by the detector of the x-ray photon number as a function of position of the inner portion of the beam represents the attenuation by the object of photons above the k-edge of the contrast agent while the recording by the detector of the x-ray photon number for the outer portion of the beam represents the attenuation by the object of photons that are below the k-edge of the contrast agent. For materials within the object that are composed of atoms that are different from the absorbing atom of the contrast agent, the relative attenuation of photons contained in the two regions of the x-ray beam are basically identical. Therefore, a suitably-normalized, numerical subtraction of the two images obtained by the scan will be to first order zero everywhere except where the contrast agent is present. This technique provides a highly sensitive and low dose modality for imaging of contrast agents or specific atomic materials within an object provided that they differ significantly in atomic weight from the overall matrix of the object.

More specifically, FIG. 3A shows beam region 12 as provided by the system of FIG. 2B. The laser Compton x-ray source is configured so that beam region 12 has an energy that is above the k-edge of a material of interest in the object 50. Note that and example object 50 can be human tissue but of course other object can be placed in the beam. Beam region 12 propagates in the z direction through the object 50 and onto an x-ray detector 52. Such detectors are known in the art. Again, the figure depicts the object to be a person. In such cases, the person may ingest or be injected with a contrast agent containing the material of interest. The person or object can be raster scanned in the x-y plane to collect and obtain an image of the above k-edge x-ray photons that are not absorbed by the contrast agent. FIG. 3B shows the beam 14 as provided by the system of FIG. 2C. In this case, only beam region 14 is allowed to propagate through the object 50 and onto the x-ray detector 52. The person or object can be raster scanned in the x-y plane to collect and obtain an image of the below k-edge photons that pass through the object. As discussed herein, a suitably-normalized, numerical subtraction of the two images obtained by the scans will be to first order zero everywhere except where the contrast agent is present.

One specific example is angiography in which an iodine-containing contrast agent is injected into the blood stream. Iodine is atomic number 53 and has a k-edge absorption energy of 33.2 keV. The surrounding tissue is generally composed of lower atomic weight atoms, e.g., carbon, oxygen, hydrogen etc. These atoms do not vary significantly in their attenuation at or around the 33.2 keV k-edge of iodine. Thus a 2-color, subtraction image with a laser-Compton x-ray beam tuned to the iodine k-edge will produce a high contrast map of the location of iodine and consequently a high contrast image of the blood vessels containing the iodine.

The following are some exemplary variations of two-color, subtraction imaging with laser-Compton x-ray sources. The invention is not limited to these examples.

1. FIG. 4A illustrates an embodiment of a two pixel modality of the present invention. FIG. 4B illustrates an embodiment of a two pixel detector for use with the two pixel modality of FIG. 4A. In this instantiation, the detector contains only two detection regions; one that subtends the on-axis, high-energy region of the beam (beam region 12) and one that subtends the desired, surrounding, low-energy region of the beam (beam region 14). Such a detector may be constructed by the same micro-fabrication techniques used to create silicon x-ray diodes. Alternatively a 2-D detector such as an x-ray CCD may be used if the pixels of the detector are binned into two groups associated with the two regions. The advantage of this modality is potential simplicity of the detector and data reduction. Spatial resolution of the image however will be limited to the spatial extent of the beam in the two regions. FIG. 4A includes a high Z tube 70 between the object 50 and the two pixel x-ray detector 56. The high Z tube 70 is matched to the diameter of the beam to preclude scattered x-rays from reaching the detector 54. FIG. 4B shows the face of the two pixel x-ray detector 54. The inner, round pixel area 64 records "above" k-edge photons and the outer, annular pixel region 66 records "below" k-edge photons.

Figure 5B:
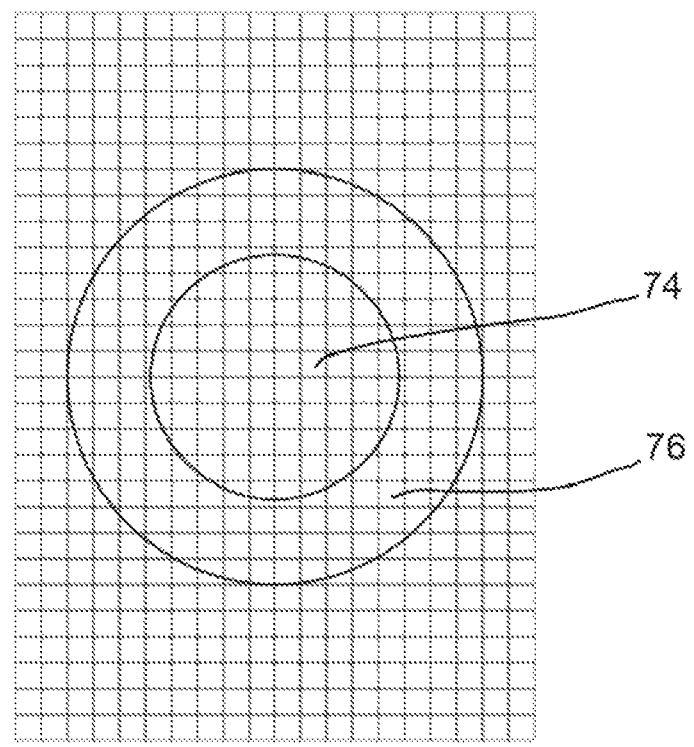
FIG. 5B illustrates a detector for use with the embodiment of FIG. 5A where the detector consists of a 2-D array of pixels which subtends both the high energy and low energy portion of the beam.

2. FIG. 5A illustrates a "many pixel" modality embodiment of the present invention. FIG. 5B illustrates the face of an exemplary detector used with the embodiment of FIG. 5A where the detector consists of a 2-D array of pixels which subtends both the high energy and low energy portion of the beam. The elements of FIG. 5A are identical to those of FIG. 4A, and such elements are identically numbered, except that this embodiment uses the 2-D x-ray detector array 56. In this instantiation, the detector is a high-resolution 2-D detector such as (but not limited to) a 2-D x-ray CCD detector. The spatial resolution of the image will be determined by the spacing of the CCD elements and the source size of the laser-Compton x-ray source. The numerical registration and subtraction of the image will require more computations than variation 1 above. In the embodiments that utilize an array type of detector, only the pixels that are completely within the high energy region are used to calculate the energy level of that region. The same is true of the lower energy region. Only the pixels that are completely within the area of the array that detects the lower energy beam region are used to calculate the lower beam energy level. The pixels that are not completely within the respective beam region are discarded in the calculation. FIG. 5B shows the face of the detector array. The inner pixel area 74 records "above" k-edge photons and the outer pixel region 76 records "below" k-edge photons.

3. In an embodiment utilizing an equal area modality, the area of the two x-ray regions are set to be the same. This is either accomplished by apertures placed in the beam to limit the extent of the outer surrounding beam or by limiting the extent of the detector subtended by the outer region of the beam such that the area illuminated by this portion of the beam is equal to the area illuminated by the inner portion of the beam. This mode reduces the computational overhead associated with image reconstruction and assures that one portion of the beam does not sample the object any more than the other.

4. In an embodiment utilizing an equal flux modality, the size of the surrounding region is set so that the total number of photons contained in this region equals that of the on axis region. The images recorded by the two regions are naturally normalized and thus simplifying the image reconstruction.

Figure 6B:
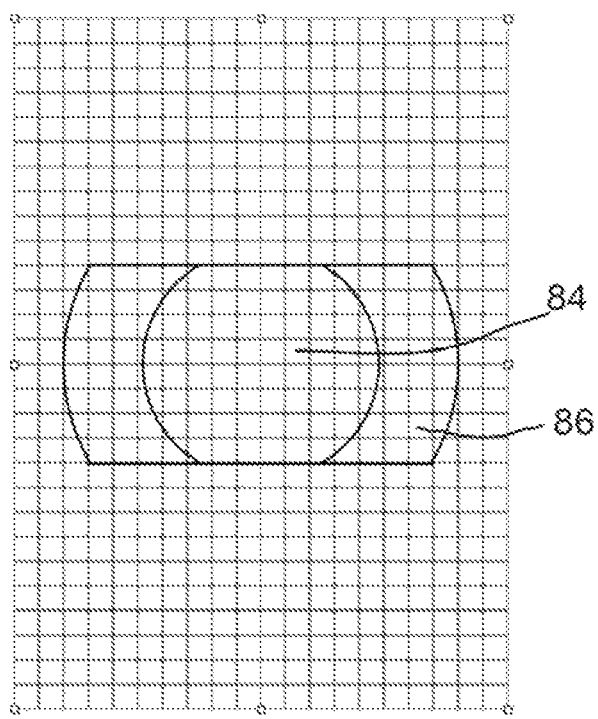
FIG. 6B illustrates a detector for use with the embodiment of FIG. 6A.

5. FIG. 6A illustrates an "equal spatial dimension" modality embodiment of the present invention where the beam is passed through a slit so that either the horizontal or vertical dimensions of the beam portions are equal. FIG. 6B illustrates a detector 56 for use with the embodiment of FIG. 6A. Elements identical to those of FIG. 5A are identically numbered. In this instantiation, the entire beam is passed through a slit aperture 80 so that the surrounding region is limited in either the horizontal or vertical dimension to be the same width as the on-axis high energy x-ray region. This simplifies the scanning and data retrieval algorithm. FIG. 6B shows the face of the detector array. The inner pixel area 84 records "above" k-edge photons and the outer pixel region 86 records "below" k-edge photons.

Figure 7A:
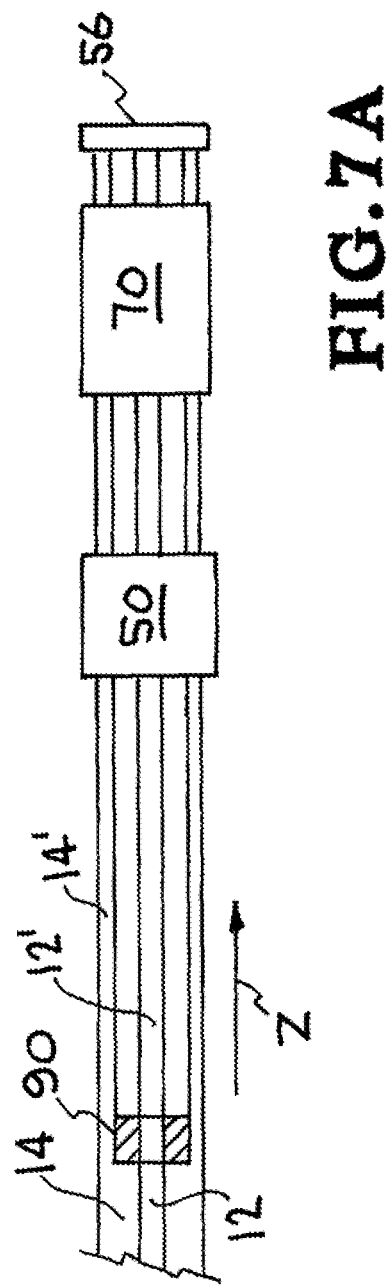
FIG. 7A illustrates a "discontinuous annular beam" modality embodiment of the present invention.
Figure 7B:
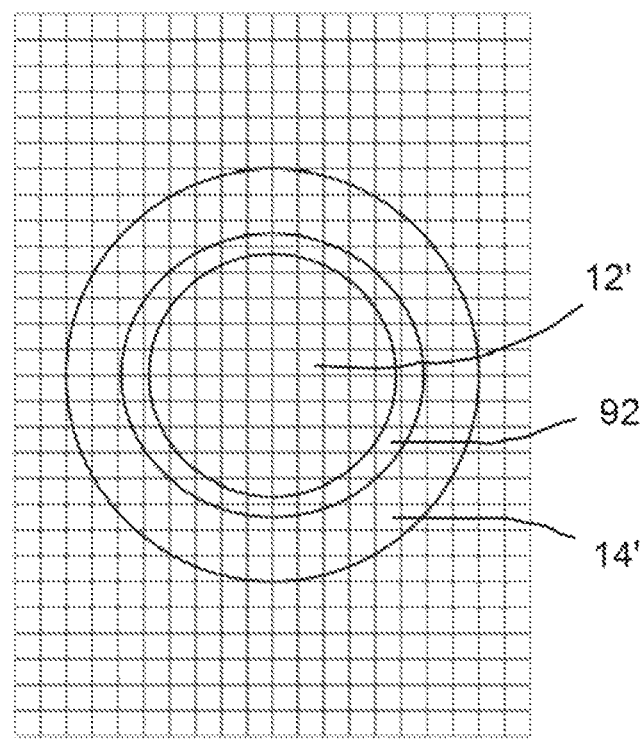
FIG. 7B illustrates a detector for use with the embodiment of FIG. 7A.

6. FIG. 7A illustrates a "discontinuous annular beam" modality embodiment of the present invention. Elements identical to the embodiment of FIG. 5A are identically numbered. An annular aperture 90 is placed such that it produces an area 92 of no photons between beam region 12' and beam region 14'. FIG. 7B illustrates the face of a detector for use with the embodiment of FIG. 7A. The laser-Compton x-ray beam profile for linear polarized laser light is oval in shape. In this modality a round annular obscuration is placed in the beam to create the two distinct spectral regions of the beam. This is the simplest method for physically creating the separate beam areas.

7. FIG. 8A shows a "dithered detector" modality according to the present invention. Elements identical to the embodiment of FIG. 5A are identically numbered. FIGS. 8B-D show various positions of a detector in the beam of the embodiment of FIG. 8A. In this instantiation a single pixel detector 58 which consists of an x-ray diode and collimating aperture/tube subtends an area equal to the high energy portion of the x-ray beam. With the x-ray beam held fixed, the detector is dithered in the plane transverse to the propagation direction of the laser so that it alternatively intercepts the low energy portion and the high energy portion of the beam. FIG. 8B shows the detector 58 in the "up" position so that it intercepts only "below" k-edge photons 14. FIG. 8C shows the detector in the "middle" position so that it intercepts only "above" k-edge photons 12. FIG. 8D shows the detector in the "down" position so that it intercepts only "below" k-edge photons 14. This modality enables use of the fastest possible, simplest possible and/or least expensive detectors to construct an x-ray image. It does, however, increase the dose seen by the object by a factor of 2.

8. FIGS. 9A and 9B show a "dithered aperture" modality according to the present invention. Elements identical to the embodiment of FIG. 5A are identically numbered. In this instantiation a fixed detector 60 that subtends the entire area of both beam regions 12 and 14 is used. After the laser-electron interaction point that produces the x-ray beam and before the object, a movable aperture or beam block 110 is placed in the beam. The role of this aperture is to block in an alternating manner the on-axis high-energy portion of the beam and the surrounding low-energy portion of the beam in synchronism with the pulsed output of the laser-Compton x-ray source. FIG. 9A shows the aperture 110 in the "middle" position so that it passes only beam region 12 which consists of high energy x-rays. FIG. 9B shows the aperture 110 in the "up" position so that it passes only beam region 14 which consists of low energy x-rays. This alternating beam block could be constructed in a number of ways. For example by placing a high-Z material of the appropriate shape on a low-Z disk and rotating the disk in the beam at a rate that places the aperture such that the desired beam portion is blocked and the desired beam portion is allowed to transmit. This modality alternatingly records the above k-edge and below k-edge attenuation of the object. This modality enables use of fast, simple and/or cheap detectors to construct an x-ray image and does not expose the object to any higher dose than instantiations 1 thru 6 above. It does however take 2× longer to accumulate an image with this modality. It should be noted that both the dithered detector and dithered aperture modality could be combined and would enable use of a smaller area x-ray detector. In principle the scatter reduction tube 70 shown in this disclosure could also be dithered in synchronism with the aperture and/or detector and in doing so would allow for a smaller tube diameter and greater discrimination of unwanted, scattered x-ray photons emerging from the back surface of the imaged object.

9. An embodiment of the invention is referred to as a double annulus modality. In this instantiation, the on axis portion of the beam is not used but rather two annular portions of the beam are selected. Because the energy of the spectral content of the beam decreases as a function of angle, it is possible to select an inner annulus that contains higher energy photons than the outer annulus. As described above, these two annuli can be used to construct a 2-color subtraction image. There is no intrinsic advantage to this modality except that the two beams have similar form factors. In this embodiment, although the inner annulus is not centered on the optical axis of the x-ray beam, the source power can be turned up so that the inner annulus has an energy level that is above the k-edge of a material of interest.

10. In another embodiment, no aperture is used to constrain the extent of the laser-Compton beam and the full beam is incident upon the object to be imaged. By removing the object from the beam path, the profile of the full laser-Compton beam may be obtained on the downstream 2-D detector. Pixel location on this detector will be correlated with a specific range of x-ray photon energies and may then be used as described above to produce a 2-color subtraction radiograph. This modality is suited to applications in which the laser-Compton source is scanned across the object and for which a moving aperture to limit the outer beam extent would be impractical.

11. In another modality, a time-gated detector is used to record the ballistic photons above and below k-edge photons that reach the detector and to discriminate against any photons scattered by the object under interrogation that might also reach the detector location. The gate time of the detector must be of order the duration of the laser-Compton x-ray pulse, i.e., a few to a few 10's of picoseconds. The time-gate must be synchronized to the x-ray pulse. This modality not only enables higher contrast for a fixed dose by eliminating the background scattered x-ray photons from the image but also improves the subtracted image by insuring that only the ballistic photons of the correct energy are present in the respective above and below k-edge images. This modality may be accomplished with either a gated 2-D detector or a gated single pixel detector.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

I claim:
1. A method, comprising:
providing an x-ray beam from a laser-Compton x-ray source, wherein said x-ray beam is produced by colliding only one laser beam with an electron beam wherein said x-ray beam includes a first beam region having an energy that is greater than the k-shell absorption edge of a test element and wherein said x-ray beam further includes a second beam region having an energy that is less than the k-shell absorption edge of said test element;

directing said x-ray beam onto a first location on an object;
detecting first energy of said first beam region and second energy of said second beam after portions of each have transmitted through said first location;
calculating the difference between said first energy and said second energy pattern; and
displaying said difference.

2. The method of claim 1, wherein the step of displaying said difference comprises displaying said difference either as data or an image.

3. The method of claim 1, further comprising repeating the steps of claim 1 a plurality of times at different locations.

4. The method of claim 1, further comprising repeating the steps of claim 1 a plurality of times by rastoring the relative locations one to another of said object and said x-ray beam.

5. The method of claim 1, wherein said x-ray beam is apertured between said source and said object such that only said first beam region and said second beam region of said x-ray beam propagate onto said object.

6. The method of claim 5, wherein only one of said first beam region or said second beam region is allowed to propagate onto said location at a time, and then the other of said first beam region or said second beam region is allowed to propagate onto said location.

7. The method of claim 1, further comprising eliminating, with a high Z tube, at least a portion of x-rays that have been scattered by said object from being detected.

8. The method of claim 1, wherein the step of detecting is carried out with an x-ray detector having an inner region for detecting said first energy and an outer region for detecting said second energy.

9. The method of claim 1, wherein the step of detecting is carried out with a 2-D x-ray detector array.

10. The method of claim 9, wherein only pixels of said 2-D detector array that are fully covered by said first energy are used to calculate said first energy and only pixels of said 2-D detector array that are fully covered by said second energy are used to calculate said second energy.

11. The method of claim 1, further comprising passing said x-ray beam through a slit such that one dimension of said first beam region and second beam region are the same.

12. The method of claim 1, further comprising aperturing said x-ray beam such that there is a distinct area between said first beam region and said second beam region where there are no photons of either region.

13. The method of claim 1, wherein the step of detecting is carried out with an x-ray detector having an area that is small enough so that it can detect only one of said first energy or said second energy at a time, the method further comprising dithering said detector between said first beam region and said second beam region.

14. The method of claim 1, wherein said first region and said second region are aperture to have about the same area.

15. The method of claim 1, wherein the size of said second region is set so that the total number of photons contained in said second beam region equals that of said first region.

16. The method of claim 1, wherein an aperture is placed in the path of said beam prior to said object, wherein said aperture is configured to allow passage of only one of said first beam region or said second beam region, the method further comprising dithering said aperture to allow first one beam region and then the other.

17. An apparatus, comprising:
a laser-Compton x-ray source, wherein said x-ray beam is produced by colliding only one laser beam with an electron beam for providing an x-ray beam that includes a first beam region having an energy that is greater than the k-shell absorption edge of a test element and wherein said x-ray beam further includes a second beam region having an energy that is less than the k-shell absorption edge of said test element;
a detector configured for detecting first energy of said first beam region and second energy of said second beam after portions of each have transmitted through a first location of an object;
a processor configured for calculating the difference between said first energy and said second energy pattern; and
a display device configured for displaying said difference.

18. The apparatus of claim 17, further comprising a first aperture located between said source and said object, wherein said aperture is configured to only allow said first beam region and said second beam region to propagate onto said object.

19. The apparatus of claim 18, wherein only one of said first beam region or said second beam region is allowed to propagate onto said location at a time, and then the other of said first beam region or said second beam region is allowed to propagate onto said location.

20. The apparatus of claim 17, further comprising a high Z tube placed between said object and said detector, wherein said high Z tube is configured for eliminating at least a portion of x-rays that have been scattered by said object from being detecting.

21. The apparatus of claim 17, wherein said detector comprises an inner region for detecting said first energy and an outer region for detecting said second energy.

22. The apparatus of claim 17, wherein said detector comprises a 2-D x-ray detector array.

23. The apparatus of claim 17, further comprising a slit aperture positioned between said source and said object, wherein said slit is configured such that one dimension of said first beam region and said second beam region are about the same.

24. The apparatus of claim 17, further comprising an annulus placed within said beam for aperturing said x-ray beam such that there is a distinct area between said first beam region and said second beam region where there are no photons of either region.

25. The apparatus of claim 17, wherein said detector has an area that is small enough so that it can detect only one of said first energy or said second energy at a time, said apparatus further comprising means for dithering said detector between said first energy region and said second energy region.

26. The apparatus of claim 17, further comprising an aperture placed in said beam to perform a function selected from the group consisting of (i) setting said first region and said second region to have about the same area, (ii) setting the size of said second region so that the total number of photons contained in said second beam region equals that of said first region and (iii) allowing passage of only one of said first beam region or said second beam region wherein the apparatus further comprises means for dithering said aperture to allow first one beam region and then the other.

27. A method for 2-color radiography with an x-ray beam produced by a laser-Compton x-ray source, the method comprising:
providing an x-ray beam from a laser-Compton x-ray source, wherein said x-ray beam is produced by colliding only one laser beam with an electron beam, wherein said x-ray beam includes a first beam region having an energy that is greater than the k-shell absorption edge of a test element and wherein said x-ray beam further includes a second beam region having an energy that is less than the k-shell absorption edge of said test element;

directing said first beam region onto a first location of an object;

obtaining a first energy measurement of a portion of any photons from said first beam region that propagate through said object at said first location;

directing said second beam region onto said first location;

obtaining a second energy measurement of a portion of any photons from said second beam region that propagate through said object at said first location;

calculating the difference between said first energy measurement and said second energy measurement; and displaying said difference.

28. An apparatus for 2-color radiography with an x-ray beam produced by a laser-Compton x-ray source, the method comprising:

a laser-Compton x-ray source, wherein said x-ray beam is produced by colliding only one laser beam with an electron beam for providing an x-ray beam, wherein said x-ray beam includes a first beam region having an energy that is greater than the k-shell absorption edge of a test element and wherein said x-ray beam further includes a second beam region having an energy that is less than the k-shell absorption edge of said test element;

a detector configured and positioned for obtaining a first energy measurement and a second energy measurement, wherein said first energy measurement is of a portion of any photons from said first beam region that propagate through an object at a first location on said object and wherein said second energy measurement is of a portion of any photons from said second beam region that propagate through said object at said first location;

means for calculating the difference between said first energy measurement and said second energy measurement; and means for displaying said difference.

* * * * *